United States Patent [19]

Streifer et al.

[11] Patent Number: 4,826,269
[45] Date of Patent: May 2, 1989

[54] DIODE LASER ARRANGEMENT FORMING BRIGHT IMAGE

[75] Inventors: William Streifer, Palo Alto; Donald R. Scifres; Gary L. Harnagel, both of San Jose, all of Calif.

[73] Assignee: Spectra Diode Laboratories, Inc., San Jose, Calif.

[21] Appl. No.: 109,824

[22] Filed: Oct. 16, 1987

[51] Int. Cl.[4] .................... G02B 5/32; G02B 27/18; F21K 5/00
[52] U.S. Cl. .................... 350/3.72; 350/167; 362/252; 362/800
[58] Field of Search .............. 350/167, 3.72; 362/800, 362/252

[56] References Cited

U.S. PATENT DOCUMENTS

| | | | |
|---|---|---|---|
| 4,253,723 | 3/1981 | Kojima et al. | 350/3.72 |
| 4,428,647 | 1/1984 | Sprague et al. | 350/167 |
| 4,729,070 | 5/1988 | Chiu | 362/804 |

FOREIGN PATENT DOCUMENTS

| | | | |
|---|---|---|---|
| 485381 | 2/1952 | Italy | 362/804 |
| 62-65013 | 3/1987 | Japan . | |
| 0510162 | 4/1976 | U.S.S.R. | 362/804 |

OTHER PUBLICATIONS

Horne, D. F. "Optical Production Technology" pp. 121 & 194, Crane Rossak & Co., Inc. N.Y.

W. Streifer et al., "Phased Array Diode Lasers", Laser Focus/Electro-Optics, Jun., 1984.

*Primary Examiner*—Bruce Y. Arnold
*Attorney, Agent, or Firm*—Thomas Schneck

[57] ABSTRACT

A plurality of diode lasers is focussed onto a single region by arranging the diodes at equally spaced locations on a first arc. Each diode laser emits light in a slit-like pattern which is characterized by orthogonal axes. In a first group of cylindrical lenses, one associated with each diode laser, each lens has a refractive surface having an axis parallel to one of the emitting axes of the laser and refracts light to a focal region of defined dimensions. Each cylindrical lens is disposed along a second arc having a circular center common with the first arc. A second group of cylindrical lenses, one associated with each laser, is also disposed on a circular arc, concentric with the other arcs, but the second group has a refractive axis perpendicular to the first refractive axis. The second group of cylindrical lenses acts upon the second axis of the source image, focussing it to the common focal region. The first and second cylindrical lens groups may be combined into a toric surface within a single lens. The cylindrical lenses may either be individual lenses, or may be combined into a lenticular array. The lenses may be simple cylindrical refractive lenses, Fresnel lenses, or holographic lenses. A bright image of the source is formed at the common focal region. The diode lasers and cylindrical lenses may be arranged in three dimensions to produce very high optical power densities.

28 Claims, 3 Drawing Sheets

DIODE LASER ARRANGEMENT FORMING BRIGHT IMAGE

TECHNICAL FIELD

The invention relates to diode laser illumination sources with divergent beams which may be combined to form a bright image.

BACKGROUND ART

Many times it is desirable to focus a plurality of light sources into a spot, so that a bright source image is formed. For lasers, such applications arise in laser fusion, laser surgery and cutting applications, and in communications.

For conventional lasers with beams of circular symmetry, standard optical lenses may be used to form bright spots. A problem arises, however, in attempting to focus a plurality of diode lasers onto a small spot or zone, i.e. as small as 20 microns on a side of a square entrance aperture, but possibly larger depending on the system specifications. In a diode laser or diode laser bar, light emerges from an active layer or region at a cleaved facet or edge of the diode in a slit-like pattern which is oblong in character. Typical dimensions for a slit in a laser bar might be one micron high by 400 microns wide, with light emerging at a large divergent angle from the small dimension and a significantly lesser divergent angle from the large dimension. Construction of a double-heterostructure, phased-array diode laser with an emitting geometry similar to the one mentioned is disclosed in an article entitled "Phased Array Diode Lasers" by W. Streifer in *Laser Focus*. June, 1984. In this application the term "diode laser" will be used interchangeably with "laser bar" or "laser array".

The small size of the diode laser and the wide divergent beam makes the problem of focusing a plurality of beams unlike the same problem associated with conventional lasers. Moreover, to focus an image of the narrow source dimension on a spot with an aperture of 200 microns in diameter, for example, magnification would be required for the narrow slit dimension mentioned above, while reduction would be required for the large slit dimension.

In Sprague et al. U.S. Pat. No. 4,428,647 disclose a plurality of diode lasers imaged to a plurality of spots through a pair of lenses. A first lens system is a lenticular array which changes the angle of divergence from a wide angle to a narrow angle for each diode laser. In this system, a lens element of the lenticular array is associated with each diode laser. A second lens acts as an objective, focusing light to an image plane where a plurality of spots are formed, one corresponding to each diode. Note that total convergence of the beams is not achieved.

An object of the invention is to devise an optical arrangement for focusing a plurality of diode lasers into a single bright focal region.

A further object is to devise a laser arrangement for concentrating a high amount of energy in a small zone.

DISCLOSURE OF THE INVENTION

The above object was achieved by aligning a plurality of beams from diode lasers in a first circular arc with output beams aimed radially toward a common focal region or zone. Lens elements, capable of focusing the oblong beams from the lasers were placed in a radially inward, concentric, second arc, with the lens elements having a common focal region. The lens elements may be either individual lenses or a lenticular array, and the individual elements or the individual elements of the lenticular array may be discrete lenses, compound discrete lenses, a holographic lens (formed by analog or digital means), or Fresnel lens, so long as beams are brought to the same focal region without significant loss of brightness. The lens elements convert divergent output beams from diode lasers to convergent beams, aimed at a region which may be on the order of 200 microns in diameter. By focusing a number of beams on a small region, the brightness of the individual lasers is preserved and the focal region itself is bright. If the lens array is extended in three dimensions, it is even possible to more intensely illuminate a region or a line formed by a locus of bright regions. The line may be either a straight line or a curve, such as a circle. The brightness may be converted to heat and a three dimensional laser array may be used for applications where high power gas or solid state lasers are used.

BEST MODE FOR CARRYING OUT THE INVENTION

Figure 1:
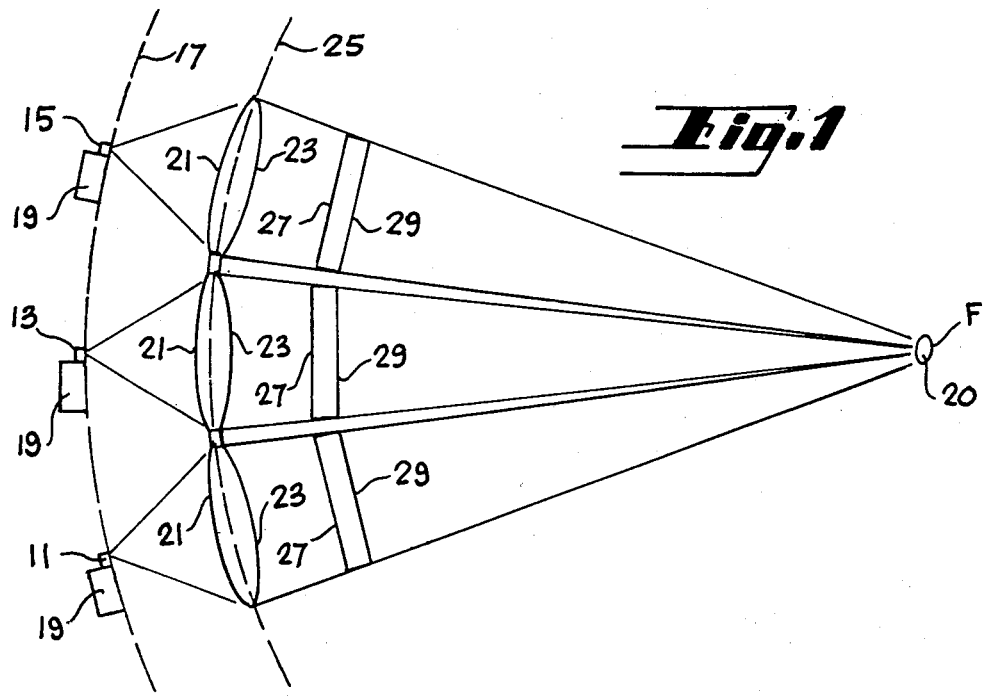
FIG. 1 is a plan view of a plurality of diode lasers and focusing optics disposed in a circular arc in accord with the present invention.

With reference to FIG. 1, diode lasers 11, 13 and 15 are shown spaced about a first circular arc 17 having a center F in a circular zone 20, which is a desired focal region of defined diameter, e.g. 200 microns. Each diode laser is mounted on a supporting mounting plate 19 which supplies power, cooling and mechanical support. The diode lasers themselves need not be on a circular arc. Alternatively, the beams from the lasers can be deflected to lie on an arc after deflection from another location, for example, by a prism. The diode lasers may be individual diodes, or preferably laser bars, for example, of the type described in the above mentioned article entitled "Phased Array Diode Lasers" by W. Streifer et al. Such lasers have C.W. output power levels of a few watts and newer versions have greater power levels.

Light is emitted from a diode laser in a divergent slit-like pattern. The pattern has an oblong appearance and lacks the circular symmetry associated with rod and tube sources. If the vertical height of the source image at the diode laser output is 1 micron and the vertical height of the target region is 200 microns the vertical magnification may be as large as (or even exceed) 200, although a more practical magnification might be 40. On the other hand, if the horizontal width of the source image is 400 microns and the horizontal width of the target region is 200 microns, the required image reduction in the horizontal direction is two.

In order to convert the divergent beam to a convergent beam, to be focused at a region, two different perpendicular refractive axes are needed, one for each axis of the oblong slit image. Refractive surfaces 21 and 23 form a refractive axis of a first orientation and are associated with each diode laser and aligned along an arc 25 which is concentric with the first arc 17. The lens formed by the refractive surfaces 21 and 23 may be termed a vertical lens since the direction of curvature of the refractive surfaces is designed to operate on the vertical component of the source image. The aggregation of lenses along the circular arc 25 may be connected together as a lenticular array, or may be separate lenses, or may be Fresnel lenses, or may be holographic lenses.

The degree of curvature of the refractive surfaces should be such to focus the source image at a distant focal region with the desired magnification. The lens itself is a cylindrical lens with no curvature in the horizontal direction. If a 60° collection cone from the lasers is desired, the angle of each laser output, i.e. source image, entering the vertical aperture is 1.5° at 40:1 magnification. This means that about 13 diode lasers could be placed about the arc of a circle and still emit into a 20° output cone in the vertical direction.

A second group of lenses has a refractive axis of a second orientation, perpendicular to the first orientation. Each lens is associated with a diode laser. Refractive surfaces 27 and 29 refract light in the horizontal direction, perpendicular to the direction of the refractive surfaces 21 and 23. Since the horizontal component of the source image is less divergent than the vertical component, refractive correction of the source image is not as great in the horizontal direction. Nevertheless, the image of the source must be focused to the same focal area as the vertical component of the image. For example, each diode laser may emit a beam with a cone angle of about 10°. If the allowed collection angle of the horizontal object aperture or region is 20°, a 2:1 reduction in the width of the horizontal source image of each laser is required. A 400 micron wide emitting source image can therefore pass through the 200 micron aperture of the target focal region.

The lenses formed by the refractive surfaces 27 and 29 may be connected together in a lenticular array, sometimes known as a "fly's eye" lens. The combination of refractive surfaces for each diode laser is termed a "lens element". In other words, a lens element includes refractive correction for both the vertical and horizontal image components. The two lenses can be combined in a single lens having toric surfaces, i.e. refractive surfaces whose curvature is mutually orthogonal. The lenses may also be formed by patterning a substrate or by introducing index variations to produce Fresnel lenses or holographic lenses with the same or similar effects.

Figure 2A:
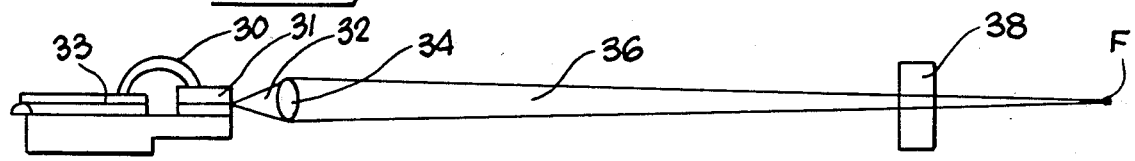
FIG. 2A is a side plan view of a diode laser array mounted on a support plate with focusing optics.

FIG. 2A shows the diode laser 31 supported on mounting plate 33 and electrically connected by wires 30. Diode laser 31 emits beam 32 which is intercepted by a first cylindrical lens 34, having a refractive axis parallel to one of the axes of the oblong slit light emission image. The beam 36, emerging from lens 34 is intercepted by cylindrical lens 38, having a refractive axis perpendicular to the first refractive axis, but nonrefractive to beam 36. The two lenses form a two-axis lens element which refracts the source image to focal region F. The source image has a nominal vertical dimension, $I_V$, of one micrometer. A beam 32 carrying this image diverges from the slit at an angle, $\theta_V$, prior to entry into lens 34. This lens forms the beam into a vertically convergent beam 36 having an angle $\theta_V/40$. The beam passes through cylindrical lens 38 without refraction in the vertical direction. The vertical dimension of the forcal region image $I_V'$ is 40 micrometers, a forty fold vertical increase in image size.

Figure 2B:
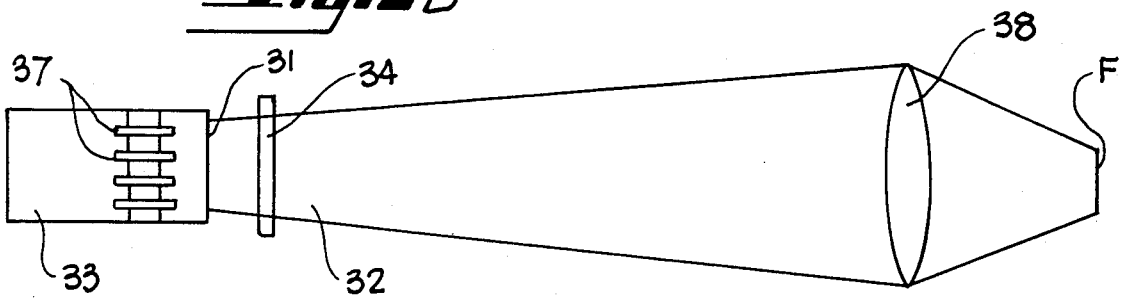
FIG. 2B is a top plan view of the diode laser array and focusing optics of FIG. 2A.

In FIG. 2B, the top of the plate 33 is shown covered by an insulative layer 35 upon which one or more conductors 37 may be disposed for purposes of communicating power to diode laser 31. Each conductor can supply power to a number of laser diodes. A metallic coating may be used to dissipate heat from the lasers. The source image has a nominal horizontal dimension, $I_H$, of 0.5 cm from a plurality of diode lasers. The beam 32 carrying this image diverges from the source slit at an angle, $\theta_H$, prior to entry into lens 34. This lens is nonrefractive in the horizontal plane and so the beam continues to lens 38 which is refractive in the horizontal plane. Lens 38 causes convergence of the beam toward focal region at an angle equal to 2.5 $\theta_H$. The horizontal dimension of the focal region image $I_H'$ is 0.2 cm, a decrease in horizontal image size by 2.5 times.

Figure 3:
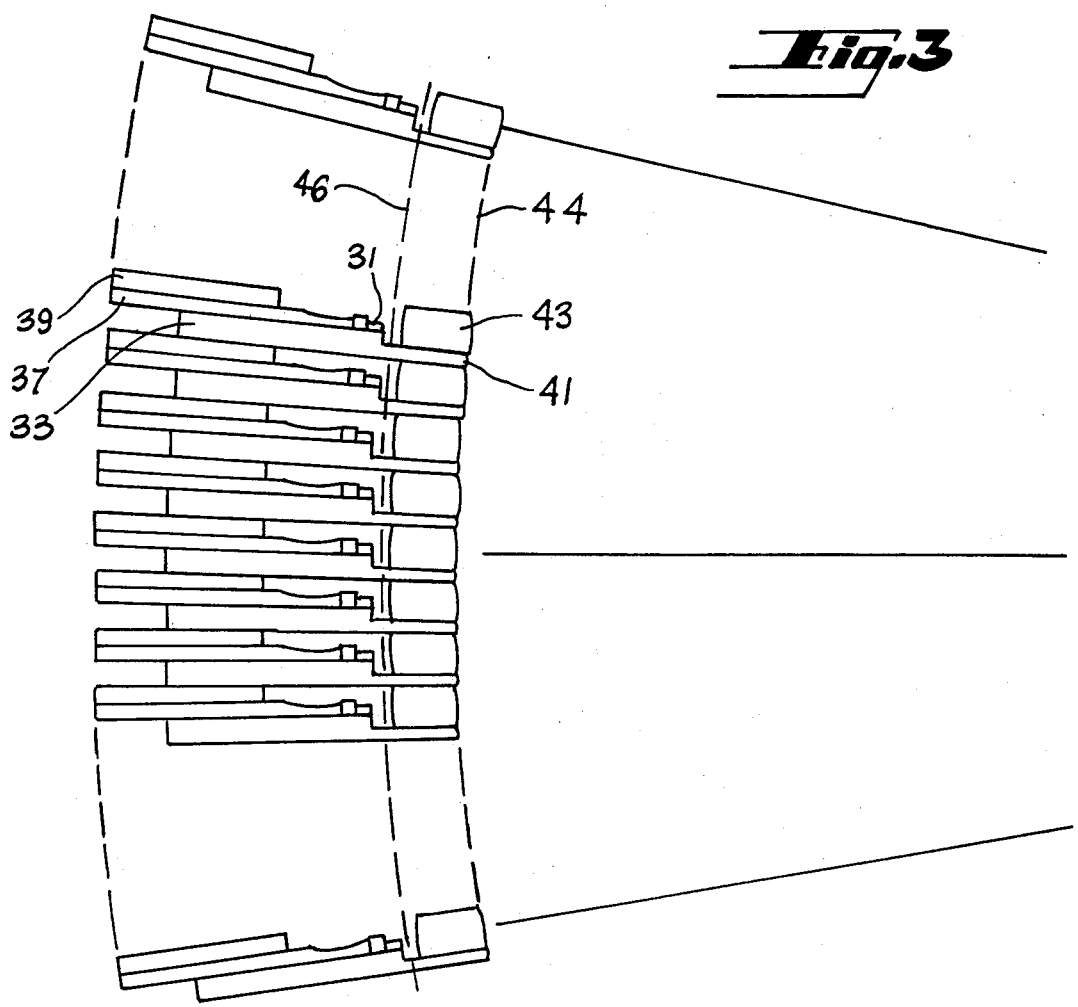
FIG. 3 is a plan view of a plurality of diode lasers each mounted on a card or plate in combination with a lens.

In FIG. 3, a plurality of mounting plates 33 of the type shown in FIG. 2 is disposed carrying diode lasers or laser bars 31 with the lasers having output beams lying on a common circular arc 46 with the center of the circle being a focal point discussed below. In addition to the conductive layer 37 carried by each plate an insulative spacer 39 is used to connect adjacent plates together with proper spacing and alignment. The plate 33 has a nose portion 41 which is used to support a toric lens element 43. The lens element focuses light from the diode laser at a region whose center is the focal point previously mentioned. The lens elements lie along a circular arc 44, concentric with the arc on which the diode lasers are disposed. The lens elements focus the beam from each diode laser so that the beams converge upon the focal region either in an overlapping or in a non-overlapping fashion as required by the application. If a second layer is stacked atop the layer shown in FIG. 3 the focal region may be different or the same as the focal region of the underlying layer. If the same focal region is selected, the lasers would be disposed along a curve perpendicular to the curve shown in FIG. 3. Individual lenses may be adjusted laterally and vertically to achieve the desired focal region. The focal region may be formed by side-by-side juxtapositions of individual regions or by overlap of individual regions, depending on the desired focal region size and brightness.

Figure 3A:
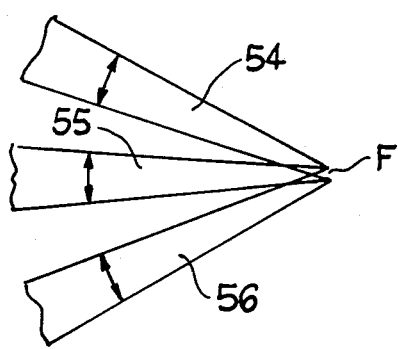
FIGS. 3A and 3B are plan views of alternate modes of focal region formation.
Figure 3B:
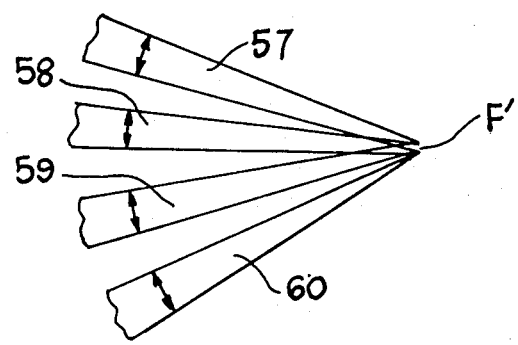

With reference to FIG. 3A, it may be seen that the focal region F is formed by overlap of beams 54, 55 and 56. The three beams coincide at a focal plane. In contrast, in FIG. 3B, the four beams 57, 58, 59 and 60 are shown to partially overlap each other in forming the focal region F'. Alternatively, instead of partially overlapping, the beams could terminate in contiguous, but nonoverlapping relationship.

Returning to FIG. 3, the lens element 43 has a thickness of 1 mm and a radius of curvature of 0.5 mm. It is situated 44 mm from the point of focus. With the distance from the laser facet 31 to the lens vertex being about 0.09 mm, the size of the image at the point of focus would be limited to about 150 μm due to spherical aberration. A perfect image of a 1 μm high line of light at the laser facet would be about 80 μm, so spherical aberration is the limiting factor (unless an acylindrical lens is employed). Even with spherical aberration, however, it is possible to couple the light from many lasers into a relatively small light guide. With mounting plates spaced 0.8 mm apart, each plate can be tilted at an angle of 1° with respect to an adjacent plate in order to face the same point of focus. With a numerical aperture of 0.3 for the light guide, about 30 lasers on mounting plates can be focused on the aperture of the light guide. Thus, whereas normal butt coupling techniques would allow only one laser to be coupled to the light guide, this embodiment allows up to 30 to be coupled with a commensurate increase in optical power density in the guide.

Figure 4:
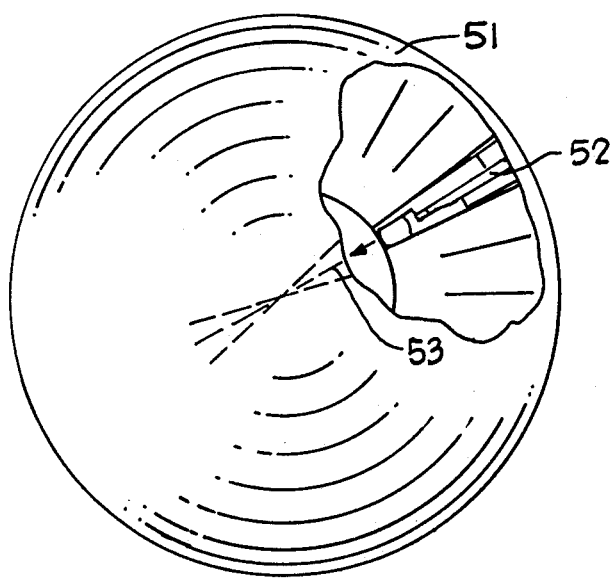
FIG. 4 is a plan view for a three dimensional toroidal configuration for diode lasers and focusing optics in accord with the present invention.

FIG. 4 is an example of three dimensional surface on which diode lasers may be disposed in accord with the present invention. In this case, all of the diode lasers are aimed at the point which is the center of the sphere 51. The lasers 52 are mounted so that their beams fall on radial lines 53 extending to the center of the sphere.

Figure 5:
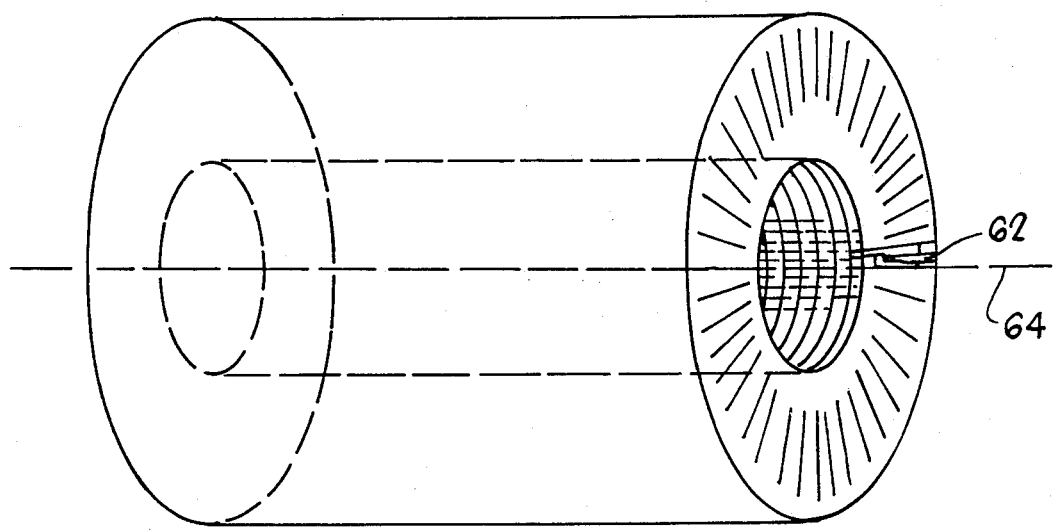
FIG. 5 is a plan view for a three dimensional cylindrical configuration for diode lasers and focusing optics in accord with the present invention.

In FIG. 5, a cylinder is shown with diode lasers 62 disposed about the outer periphery of the cylinder with beams directed inwardly along radial lines converging on the cylindrical axis 64. The axial center line 64 of the cylinder defines a locus of focal regions on which all of the beams converge.

Figure 6:
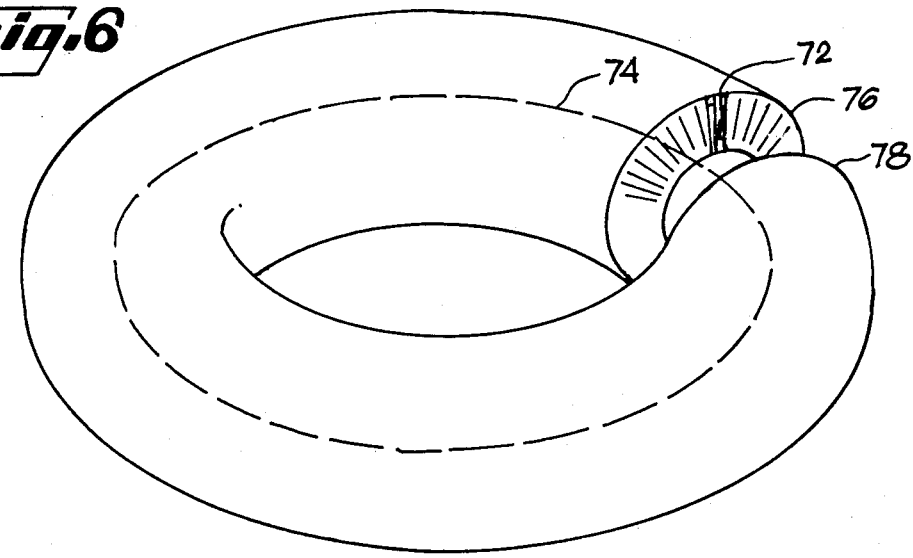
FIG. 6 is a plan view for a three dimensional toroidal configuration for diode lasers and focusing optics in accord with the present invention.

FIG. 6 illustrates a toroidal array of lasers wherein the lasers are pointed inwardly toward the center of a torus. Within the center of the torus is a line 74 containing the locus of regions on which the lasers are focused. The outside surface of the torus defines a plurality of circles, 76, 78, the circles defining the location for the diode lasers.

In each of the cases above, brightness of the laser sources is preserved to a great extent. The optical brightness may be used for heating a gas or solid at the focal point or focal line of the three dimensional configuration. The lasers may be operated either in a pulsed or CW mode and since the mounting plates point radially outwardly, they may serve as cooling fins for the three dimensional structure.

It is easiest to build the apparatus of the invention using identical lasers, having the nearly identical output beams. However, nothing limits the invention to identical lasers which would be equally spaced apart along an arc. Different types of diode lasers could be used, with different beam emitting patterns. However, different types of lenses would be selected to converge light onto the focal region without significant interaction with beams from adjacent lasers. The lasers, whether different or identical, could be disposed along an arc at spaced locations so that the convergence of the beams is in a side-by-side relationship without significant overlap. It will be realized that positioning of the lasers on a defined regular geometric surface is not critical because individual lens powers and positions could be selected to compensate for differences in source position.

We claim:

1. A diode laser arrangement forming a bright image comprising,
    a plurality of diode lasers, each having an oblong emitting area and a divergent output beam,
    a plurality of lens elements, one lens element disposed to intercept said divergent output beam for each diode laser, each lens element having means for converging said beam at an angle toward a focal region, said beams from said diode lasers and said lens elements being disposed at spaced apart distances, with said lens elements having a common focal region and the convergent angle of each beam lying in side-by-side relation to an adjacent beam said lens elements disposed along a concentric arc.

2. The laser arrangement of claim 1 wherein said plurality of lens elements are individual lenses.

3. The laser arrangement of claim 1 wherein said plurality of lens elements form a lenticular array.

4. The laser arrangement of claim 1 wherein said means for converging said beam is a cylindrical surface lens.

5. The laser arrangement of claim 4 wherein said oblong emitting area is characterized by a length and a width and said cylindrical surface images one of said length and width of the emitting area to said focal region, but does not affect the other, and a lens disposed between said lens elements and said focal region for imaging the other of said length and width of the emitting area to said region.

6. The laser arrangement of claim 1 wherein said means for converging said beam is a toric surface lens.

7. The laser arrangement of claim 6 wherein said oblong emitting area is characterized by a length and a width and said toric surface is characterized by first and second orthogonal cylindrical surfaces, including a first cylindrical surface which images one of the length and width of the emitting area to said focal region, but does not affect the other, and a second cylindrical surface which images the other of said length and width of the emitting area to said region.

8. The laser arrangement of claim 1 wherein said means for converging said beam is a Fresnel lens.

9. The laser arrangement of claim 1 wherein said means for converging said beam is a holographic lens.

10. The laser arrangement of claim 1 wherein said lasers are equally spaced along one of said arcs.

11. The laser arrangement of claim 10 wherein said stacks of laser diodes are spatially arranged in a toroidal configuration having a circular line center, and said focal regions for all stacks comprise a locus coincident with said line.

12. The laser arrangement of claim 10 wherein said stacks of laser diodes are spatially arranged in a cylindrical configuration having a straight line center, and said focal regions for all stacks comprise a locus coincident with said line.

13. The laser arrangement of claim 10 wherein said stacks of laser diodes are spatially arranged in a spheroidal configuration having a point center, with said focal regions for all stacks coincident with said point center.

14. The laser arrangement of claim 1 wherein said convergent angle of each beam forms a sector of a circle.

15. The laser arrangement of claim 1 wherein stacks of diode lasers are arranged in sectors of a circle one atop the other, said sectors being first sectors lying in radial planes relative to the circular center.

16. The laser arrangement of claim 15 wherein said stacks of diode lasers have a profile forming second sectors lying in radial planes perpendicular to the planes of said first sectors.

17. A diode laser arrangement for forming a bright image comprising,
 a plurality of diode lasers spaced apart along a planar circular arc, each laser emitting light from an active region in an oblong emitting region with a divergent output beam, each diode laser mounted on a supporting mounting plate,
 a plurality of individual lenses, one corresponding to each diode laser, supported from said mounting plate in a position intercepting said divergent output beam, each individual lens having means for converging said output beam at an angle toward a focal region, said diode lasers and said lenses having a common focal region and the convergent angle of each beam lying in side-by-side relation relative to an adjacent beam.

18. The laser arrangement of claim 17 wherein said means for converging said output beam is a cylindrical surface lens.

19. The laser arrangement of claim 18 wherein said oblong emitting area is characterized by a length and a width and said cylindrical surface images one of said length and width of the emitting area to said focal region, but does not affect the other, and a lens disposed between said lens elements and said focal region for imaging the other of said length and width of the emitting area to said region.

20. The laser arrangement of claim 19 wherein said oblong emitting area is characterized by a length and a width and said toric surface is characterized by first and second orthogonal cylindrical surfaces, including a first cylindrical surface which images one of the length and width of the emitting area to said focal region, but does not affect the other, and a second cylindrical surface which images the other of said length and width of the emitting area to said region.

21. The laser arrangement of claim 17 wherein said means for converging said output beam is a toric surface lens.

22. The laser arrangement of claim 18 wherein stacks of diode lasers arranged in sectors of a circle are arranged one atop the other, said sectors being first sectors lying in radial planes relative to the circular center.

23. The laser arrangement of claim 22 wherein said stacks of diode lasers have a profile forming second sectors lying in radial planes perpendicular to the planes of said first sectors, the total array forming a three-dimensional array.

24. The laser arrangement of claim 23 wherein said stacks of laser diodes are spatially arranged in a toroidal configuration having a circular line center, with said focal region for all stacks comprising a locus coincident with said line.

25. The laser arrangement of claim 23 wherein said stacks of laser diodes are spatially arranged in a cylindrical configuration having a straight line center, with said focal region for all stacks comprising a locus coincident with said line.

26. The laser arrangement of claim 23 wherein said stacks of laser diodes are spatially arranged in a spheroidal configuration having a point center, with said focal region for all stacks coincident with said point center.

27. The laser arrangement of claim 17 wherein said diode lasers are equally spaced along a planar circular arc.

28. A laser arrangement for forming a bright image comprising,
 a plurality of diode lasers, each having an oblong beam emitting area having first and second perpendicular emission axes and a divergent output beam, said lasers having output beams being disposed with equal spacing along an arc,
 a first refractive means having a first refractive axis aligned with the first emission axis of each beam for converging a first portion of each said beam toward a common focal region, and
 a second refractive means having a second refractive axis, perpendicular to the first refractive axis and aligned with the second emission axis of each beam for converging a second portion of said beam toward said common focal region.

* * * * *